United States Patent
Tsai et al.

(10) Patent No.: US 6,297,392 B1
(45) Date of Patent: Oct. 2, 2001

(54) GROUP IV ELEMENTS-BRIDGED METALLOCENE CATALYST FOR PREPARING BIMODAL OLEFIN POLYMERS

(75) Inventors: Jing C. Tsai, Kaohsiung; Kuang-Kai Liu, Hsinchu Hsien; Shu-Hwa Chan, Miao Li Hsien; Shian-Jy Wang, Hsinchu Hsien; Mu-Jen Young, Taipei, all of (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 08/881,897

(22) Filed: Jun. 23, 1997

(51) Int. Cl.$^7$ .................................................... C07F 17/00
(52) U.S. Cl. ............................... 556/11; 556/28; 556/31; 556/52; 556/53; 526/943
(58) Field of Search ............................... 556/11, 28, 52, 556/53, 31; 526/943

(56) References Cited

U.S. PATENT DOCUMENTS

| | | | |
|---|---|---|---|
| 5,359,102 | * 10/1994 | Inoue et al. | 526/132 X |
| 5,585,508 | * 12/1996 | Küber et al. | 556/11 |
| 5,627,117 | * 5/1997 | Mukaiyama et al. | 526/114 |
| 5,880,302 | * 3/1999 | Herrmann et al. | 556/28 |
| 5,892,079 | * 4/1999 | Wilson, Jr. | 556/28 X |

* cited by examiner

Primary Examiner—Fred Teskin
(74) Attorney, Agent, or Firm—W. Wayne Liauh

(57) ABSTRACT

A novel Group IV elements-bridged metallocene complex is disclosed which is represented by the following formula (I):

(I)

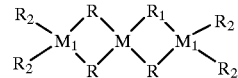

wherein R and $R_1$ are different and are independently selected from the group consisting of $\eta^5$-cyclopentadienyl group, substituted $\eta^5$-cyclopentadienyl group, indenyl group, and fluorenyl group; $R_2$ is selected from the group consisting of —$N(CH_3)_2$, —$N(C_2H_5)_2$, halogen, alkoxy, —(C=O)$NH_2$, and $C_{6-12}$ hydrocarbyl group; M is a Group IVA element; and $M_1$ is a Group IVB metal. When employing the metallocene complex to prepare olefin polymers, since it is bridged by a Group IV element, there are two catalytic sites in the single metallocene complex catalyst. Therefore, the olefin monomers can be polymerized to a bimodal olefin polymer by a single catalyst in a single reactor, resulting in lowered capital costs.

7 Claims, No Drawings

GROUP IV ELEMENTS-BRIDGED METALLOCENE CATALYST FOR PREPARING BIMODAL OLEFIN POLYMERS

BACKGROUND OF THE INVENTION

1. Field of the Invention

The present invention relates to a novel Group IV elements-bridged metallocene complex, and more particularly, to a Group IV element-bridged metallocene complex which has two catalytic sites and is capable of preparing olefin polymers having a bimodal molecular weight distribution. The Group IV elements include Group IVA elements and Group IVB metals.

2. Description of the Prior Art

Polyolefins, which include high density polyethylene (HDPE), are some of the most versatile thermoplastic resins and they have been used in a wide range of applications.

Most of the physical and mechanical properties of polyolefins, such as the high strength and high impact, stress, and puncture resistances, together with high toughness, are attributed, at least in part, to their relatively high molecular weight. However, as the molecular weight of the resin increases, the processability of the resin usually decreases.

In recent years, it has been found that polyolefins having a multimodal (typically bimodal) molecular weight distribution (MWD) can, not only retain the advantageous properties associated with high molecular weight, but also exhibit improved processability.

A bimodal MWD polymer (which can be also simply referred to as "bimodal polymer") is defined as a polymer having two distinct molecular weight distribution curves as observed from the gel permeation chromatography (GPC). In other words, a bimodal polymer can be considered as a mixture containing a first polymer with a relatively higher molecular weight and a second polymer with a relatively lower molecular weight that are blended together.

Various approaches have been disclosed for producing bimodal polyolefins. The simplest approach is to physically blend together two polymers having different molecular weights. However, this simplistic approach suffers from the problem that only with polymers that can be completely molten, homogenization can be obtained. If one of the polymers is not completely molten, then the polymer blend will be inhomogeneous. This can cause a myriad of problems.

U.S. Pat. Nos. 5,284,613 and 5,338,589 disclose a two stage polymerization process for preparing a bimodal polyolefin. In the first stage, olefin monomers are contacted with a catalyst under polymerization conditions to produce a relatively high molecular weight (HMW) polymer powder, wherein the polymer is deposited on the catalyst particles. In the second stage, the HMW polymer powder containing the catalyst is further polymerized with additional olefin monomers to produce a relatively low molecular weight (LMW) polymer much of which is deposited on and within the HMW polymer/catalyst particles from the first. The disadvantages of such a two stage process are that two reactors are needed, resulting in undesirably high capital investment.

U.S. Pat. No. 5,369,194 discloses a process for preparing bimodal polyolefins in a single reactor. The catalyst system so used includes two different transition metal catalysts supported on the same solid support material. Therefore, high and low molecular weight polymers can be formed on the same catalyst particle. The shortcoming is that procedures for preparing the solid support material which is supported with two different catalysts is complicated and difficult. Moreover, the preferable activities for the two different catalysts may be at different conditions. Therefore, when one catalyst is activated, the other catalyst may be inactivated.

SUMMARY OF THE INVENTION

The primary object of the present invention is to solve the above-mentioned problems by providing a novel metallocene complex which can be used for preparing bimodal olefin polymers using a single reactor. The metallocene complex disclosed in the present invention is bridged by a Group IV element. This creates two catalytic sites in a single metallocene complex catalyst. Thus, the olefin monomer can be polymerized into a bimodal olefin polymer using a single catalyst in a single reactor, and the catalytic activity of the catalyst is comparable to commercially available catalysts.

To achieve the above-mentioned object, a novel metallocene complex is developed in the present invention which is represented by the following formula (I):

$$R_2 \diagdown \diagup R \diagdown \diagup R_1 \diagdown \diagup R_2$$
$$\phantom{R_2}M_1 \phantom{xx} M \phantom{xx} M_1$$
$$R_2 \diagup \diagdown R \diagup \diagdown R \diagup \diagdown R_2 \quad (I)$$

wherein

R and $R_1$ are different and are independently selected from the group consisting of $\eta^5$-cyclopentadienyl group, substituted $\eta^5$-cyclopentadienyl group, indenyl group, and fluorenyl group, wherein the substituent of the substituted $\eta^5$-cyclopentadienyl group is selected from the group consisting of $C_{1-12}$ alkyl group, $C_{1-12}$ aryl group, and silyl group;

$R_2$ is selected from the group consisting of —N(CH$_3$)$_2$, —N(C$_2$H$_5$)$_2$, halogen, alkoxy, —(C=O)NH$_2$, $C_{1-12}$ hydrocarbyl groups;

M is a Group IVA element; and $M_1$ is a Group IVB metal.

DETAILED DESCRIPTION OF THE INVENTION

The present invention discloses a novel metallocene complex which is bridged by a Group IV element, and is represented by the following formula (I):

$$R_2 \diagdown \diagup R \diagdown \diagup R_1 \diagdown \diagup R_2$$
$$\phantom{R_2}M_1 \phantom{xx} M \phantom{xx} M_1$$
$$R_2 \diagup \diagdown R \diagup \diagdown R \diagup \diagdown R_2 \quad (I)$$

wherein

R and $R_1$ are different and are independently selected from the group consisting of $\eta^5$-cyclopentadienyl group, substituted $\eta^5$-cyclopentadienyl groups, indenyl group, and fluorenyl group;

$R_2$ is selected from the group consisting of —N(CH$_3$)$_2$, —N(C$_2$H$_5$)$_2$, halogen, alkoxy, —(C=O)NH$_2$, and $C_{1-12}$ hydrocarbyl group;

M is a Group IVA element, such as carbon, silicon, germanium, and tin; and $M_1$ is a Group IVB metal, such as titanium, zirconium, and hafnium.

The substituent of the substituted $\eta^5$-cyclopentadienyl group can be $C_{1-12}$ alkyl group, $C_{1-12}$ aryl group, and silyl group. Examples of the substituted $\eta^5$-cyclopentadienyl include $\eta^5$-methylcyclopentadienyl group and $\eta^5$-tetramethylcyclopentadienyl group.

According to a preferred embodiment, the metallocene complex of the present invention is prepared by first reacting $MCl_4$ with RX to obtain $MR_3Cl$, wherein M is a Group IVA element as defined earlier, R is a $\eta^5$-cyclopentadienyl group, a substituted $\eta^5$-cyclopentadienyl group, an indenyl group, or a fluorenyl group, and X is an alkaline metal.

Subsequently, the $MR_3Cl$ so obtained is reacted with $R_1Y$ to obtain $R_1MR_3$, wherein $R_1$, which is different from R, is a $\eta^5$-cyclopentadienyl group, a substituted $\eta^5$-cyclopentadienyl group, an indenyl group, or a fluorenyl group, and Y, which can be the same as or different from X, is an alkaline metal.

Finally, the $R_1MR_3$ so obtained is reacted with $M_1(R_2)_4$ to obtain the metallocene complex represented by formula (I):

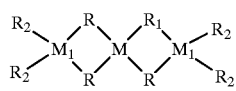

(I)

wherein

M is a Group IVB element $M_1$ is a Group IVB metal, and $R_2$ is $-N(CH_3)_2$, $-N(C_2H_5)_2$, halogen, alkoxy, $-(C=O)NH_2$, or a $C_{1-12}$ hydrocarbyl group.

Taking as an example to facilitate better understanding, when R is Cp (cyclopentadienyl), $R_1$ is methylcyclopentadienyl, $R_2$ is $NMe_2$ $[N(CH_3)_2]$, M is Sn, and $M_1$ is Zr, the above-mentioned process for preparing the metallocene complex of formula (I) can be summarized by the following three reactions:

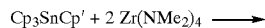

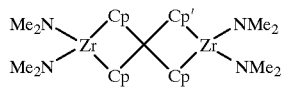

In the present invention, the Group IV elements-bridged metallocene complex can be combined with an activating cocatalyst to form a catalyst composition, which can be used for preparing olefin polymers. The group IV elements include Group IVA elements and Group IVB mentals.

The activating cocatalyst can be methyl aluminoxane (MAO), a trialkyl aluminum, a dialkyl aluminum, a salt of an inert and non-coordinating anion, or a mixture thereof.

The trialkyl aluminum can be selected from the group consisting of trimethyl aluminum, triethyl aluminum, tripropyl aluminum, trisopropyl aluminum, tributyl aluminum, and triisobutyl aluminum (TIBA).

The inert and non-coordinating anion can be a borate. Borates that are suitable for use in the present invention include N,N-dimethyl anilinium tetrakis(pentafluorophenyl) borate, triphenyl carbenium tetrakis(pentafluorophenyl) borate, trimethyl ammonium tetrakis(pentafluorophenyl) borate, ferrocenium tetrakis(pentafluorophenyl)borate, dimethyl ferrocenium tetrakis(pentafluorophenyl)borate, and silver tetrakis(pentafluorophenyl)borate.

Preferably, the activating cocatalyst is methyl aluminoxane, or a mixture of a trialkyl aluminum and a borate.

By using the catalyst composition of the present invention (containing the Group IV elements-bridged metallocene complex and the activating cocatalyst), an olefin polymer can be synthesized. One or more olefin monomers can be subjected to polymerization under polymerizing conditions in the presence of a catalytically effective amount of the metallocene complex catalyst of the present invention.

Suitable olefin monomers can be ethylene or other olefins. The polymers to be prepared by the process of the present invention can be homopolymers of ethylene, homopolymers of other olefins, copolymers of olefins, and copolymers of ethylene and other olefins. Examples of the olefins other than ethylene include those olefins having 3 to 12 carbon atoms, such as propylene, 1-butene, 1-pentene, 1-hexene, 1-octene, 1,3-butadiene and 1,5-hexadiene.

More particularly, the catalyst system disclosed in the present invention can be most advantageously used to prepare ethylene homopolymers, including high density polyethylene (HDPE) having broad, bimodal, or multimodal, molecular weight distributions for applications such as high molecular weight films and blow molding.

The novel catalyst system disclosed in the present invention can be used in slurry reaction conditions, gas phase, and solution polymerization reaction conditions. Polymerization is typically carried out at a temperature of 0° to 250° C., and from atmospheric pressure to 30,000 psig.

Since the metallocene complex of the present invention is bridged by a plurality of Group IV elements, two catalytic sites are present in every single metallocene complex catalyst. Therefore, the present invention allows the use of a single reactor and a single catalyst to produce a olefin polymer having a bimodal molecular weight distribution, thus lowering the required capital costs.

The following examples are intended to illustrate the process and the advantages of the present invention more fully without limiting its scope, since numerous modifications and variations will be apparent to those skilled in the art.

All of the following reactions were carried out under nitrogen using Schlenk technique or usual vacuum system such as a glove box. All of the solvents used were distilled to remove sodium under nitrogen and monitored by a moisture sensor. In the examples below, the following definitions are applied: Cp=$\eta^5$-cyclopentadienyl, Cp'=$\eta^5$-methylcyclopentadienyl, $CP^x$=$\eta^5$-tetramethylcyclopentadienyl, Me=methyl.

SYNTHESIS OF CATALYSTS

EXAMPLES 1

Synthesis of $Sn(Cp')_3Cp$ (Compound A)

In a 100 mL round bottom Schlenk flask, Cp'Li (2.0 g, 23.2 mmol) was dissolved in 30 mL of THF and cooled to 0° C. $SnCl_4$ (2.0 g, 7.8 mmol) in 5 mL of THF was canulated to the suspension of Cp'Li and stirred for 5 hours at room temperature. Solvent was evaporated and pentane (15 mL) was added to crash out the resulting salt to give a pale yellow solution. Pentane was evaporated and the resultant solid was re-dissolved in 30 mL of THF and cooled to 0° C. CpLi (0.56 g, 7.8 mmol) in 5 mL of THF was canulated to the solution and stirred for 4 hours at room temperature. Solvent was stripped off and toluene (20 mL) was added to crash out the salt. The final solution was concentrated to give a pale yellow solid in 70% yield.

EXAMPLES 2
Synthesis of $Sn(Cp')_3CpZr_2(NMe_2)_4$ (Compound B)

Compound A (1.0 g, 3.8 mmol) obtained from Example 1 was dissolved in 30 mL of toluene and $Zr(NMe_2)_4$ (1. 4 g, 7.6 mmol) in 5 mL of toluene was added to the solution at room temperature. After overnight stirring, the solvent was evaporated and the resultant solid was re-crystallized from pentane. The final product was a yellow solid and the yield was 72%.

EXAMPLES 3
Synthesis of $Ge(Cp')_3CP^x$ (Compound C)

In a 100 mL round bottom Schlenk flask, Cp'Li (2.0 g, 23.2 mmol) was dissolved in 30 mL of THF and cooled to 0° C. $GeCl_4$ (1.67 g, 7.8 mmol) in 5 mL of THF was canulated to the suspension of Cp'Li and stirred for 5 hours at room temperature. Solvent was evaporated and pentane (15 mL) was added to crash out the resulting salt to give a pale yellow solution. Pentane was evaporated and the resulting solid was re-dissolved in 30 mL of THF and cooled to 0° C. $Cp^xLi$ (1.0 g, 7.8 mmol) in 5 mL of THF was canulated to the solution and stirred for 4 hours at room temperature. Solvent was stripped off and toluene (20 mL) was added to crash out the salt. The final solution was concentrated to give a pale yellow solid in 75% yield.

EXAMPLES 4
Synthesis of $Ge(Cp')_3CP^xZr_2(NME_2)_4$ (Compound D)

Compound C (1.0 g, 2.6 mmol) obtained from Example 3 was dissolved in 30 mL of toluene and $Zr(NMe_2)_4$ (1.37 g, 5.12 mmol) in 5 mL of toluene was added to the solution at room temperature. After overnight stirring, the solvent was evaporated and the resulting solid was re-crystallized from pentane. The final product was a yellow solid and the yield was 65%. EXAMPLES 5
Synthesis of $GeCp_3Cp'$ (Compound E)

In a 100 mL round bottom Schlenk flask, CpLi (2.0 g, 27.7 mmol) was dissolved in 30 mL of THF and cooled to 0° C. $GeCl_4$ (1.98 g, 9.26 mmol) in 5 mL of THF was canulated to the suspension of CpLi and stirred for 5 hours at room temperature. Solvent was evaporated and pentane (15 mL) was added to crash out the salt to give a pale yellow solution. Pentane was evaporated and the resulting solid was re-dissolved in 30 mL of THF and cooled to 0° C. Cp'Li (0.79 g, 9.26 mmol) in 5 mL of THF was canulated to the solution and stirred for 4 hours at room temperature. Solvent was stripped off and toluene (20 mL) was added to crash out the salt. The final solution was concentrated to give a pale yellow solid in 72% yield.

EXAMPLE 6
Synthesis of $Ge(Cp')_3CpZr_2(NMe_2)_4$ (Compound F)

Compound E (1.0 g, 2.95 mmol) obtained from Example 5 was dissolved in 30 mL of toluene and $Zr(NMe_2)_4$ (1.58 g, 5.9 mmol) in 5 mL of toluene was added to the solution at room temperature. After overnight stirring, the solvent was evaporated and the resulting solid was re-crystallized from pentane. The final product was a yellow solid and the yield was 70%.

POLYMER SYNTHESIS

EXAMPLES 7–12

Polymerization of ethylene with or without co-monomer of 1-hexene was carried out in a 450 mL Parr high pressure reactor. The reactor vessel was thoroughly washed and dried at 110° C. for 8 hours before use. Before charging the reactants, nitrogen gas was introduced to purge oxygen from the reactor. The reactor temperature was adjusted to about 50° C.–100° C., then 200 mL of toluene, which had been distilled and degassed, was added. Thereafter, $1.5 \times 10^{-3}$ mole of methyl aluminoxane dissolved in 4 mL of toluene was charged into the reactor, followed by addition of $1 \times 10_{-3}$ mmol of the catalyst (Compound B, D, or F) dissolved in 4 mL of toluene. The amount of the cocatalyst/catalyst was set at about 2500 (mole-Al/mole-catalyst). After stirring at 50° C. for 5 minutes, ethylene gas (or ethylene gas and hexene gas) at 150 psig was introduced into he reactor and the reaction was continued for 30 minutes.

After the completion of the polymerization reaction, the ethylene pressure was released. Then 10 mL of isopropanol was charged into the reactor so as to deactivate the catalyst/cocatalyst. After filtration and drying (at 110° C. for 18 hours), a polyethylene product was obtained. The activity of the catalyst was expressed by g/g-cat.-hr (g of polymer per g of catalyst per hour).

The reaction data, including the catalytic activity, Mw (molecular weight), MWD (molecular weight distribution), were summarized in Table 1.

The foregoing description of the preferred embodiments of this invention has been presented for purposes of illustration and description. Obvious modifications or variations are possible in light of the above teaching. The embodiments were chosen and described to provide the best illustration of the principles of this invention and its practical application to thereby enable those skilled in the art to utilize the invention in various embodiments and with various modifications as are suited to the particular use contemplated. All such modifications and variations are within the scope of the present invention as determined by the appended claims when interpreted in accordance with the breadth to which they are fairly, legally, and equitably entitled.

TABLE 1

| Example | Catalyst | Temperature (° C.) | Pressure (psi) | Al/Cat. | Reaction time (min) | Comonomer (hexene) (mL) | Mw | MWD | Catalytic activity ($\times 10^4$ g/g-cat.-hr) |
|---|---|---|---|---|---|---|---|---|---|
| 7 | B | 50 | 150 | 2500 | 30 | — | 384651 | 3.6 | 2.33 |
| 8 | B | 50 | 150 | 2500 | 30 | 10 | 714416/ 12502 (bimodal)* | 15.9 | 12 |
| 9 | D | 70 | 150 | 2500 | 30 | — | 265172 | 3.7 | 6.26 |
| 10 | D | 100 | 150 | 2500 | 30 | — | 297155 | 3.6 | 9.04 |

TABLE 1-continued

| Example | Catalyst | Temperature (°C.) | Pressure (psi) | Al/Cat. | Reaction time (min) | Comonomer (hexene) (mL) | Mw | MWD | Catalytic activity (×10⁴ g/g-cat.-hr) |
|---|---|---|---|---|---|---|---|---|---|
| 11 | F | 70 | 150 | 2500 | 30 | 25 | 37248 | 3.42 | 8.22 |
| 12 | F | 70 | 150 | 2500 | 30 | — | 102953 | 3.08 | 11.51 |

*two molecular weights

What is claimed is:

1. A metallocene complex which is represented by the following formula (I)

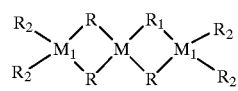

(I)

wherein
R and $R_1$ are different and are independently selected from the group consisting of $\eta^5$-cyclopentadienyl group, substituted $\eta^5$-cyclopentadienyl group, indenyl group, and fluorenyl group,
wherein the substituent of the substituted $\eta^5$-cyclopentadienyl group is selected from the group consisting of $C_{1-12}$ alkyl group, $C_{6-12}$ aryl group, and silyl group,
$R_2$ is selected from the group consisting of $-N(CH_3)_2$, $-N(C_2H_5)_2$, halogen, alkoxy, $-(C=O)NH_2$, and $C_{1-12}$ hydrocarbyl group;
M is an element selected from the group consisting of carbon, silicon, germanium, and lead; and
$M_1$ is a Group IVB metal.

2. The metallocene complex as claimed in claim 1, wherein R and $R_1$ are different and are independently selected from the group consisting of $\eta^5$-cyclopentadienyl group, $\eta^5$-methylcyclopentadienyl group, and $\eta^5$-tetramethylcyclopentadienyl group.

3. The metallocene complex as claimed in claim 1, wherein $R_2$ is $-N(CH_3)_2$ or $-N(C_2H_5)_2$.

4. The metallocene complex as claimed in claim 1, wherein M is silicon or germanium.

5. The metallocene complex as claimed in claim 1, wherein $M_1$ is selected from the group consisting of titanium, zirconium, and hafnium.

6. A process for preparing the metallocene complex of claim 1, comprising the steps of:

(a) reacting $MCl_4$ with RX to obtain $MR_3Cl$,
wherein
M is an element selected from the group consisting of carbon, silicon, germanium, and lead,
R is selected from the group consisting of $\eta^5$-cyclopentadienyl group, substituted $\eta^5$-cyclopentadienyl group, indenyl group, and fluorenyl group, and
X is an alkaline metal;

(b) reacting the $MR_3Cl$ with $R_1Y$ to obtain $R_1MR_3$,
wherein
R1, which is different from R, is selected from the group consisting of $\eta^5$-cyclopentadienyl group, substituted $\eta^5$-cyclopentadienyl group, indenyl group, and fluorenyl group, and
Y, which can be the same as or different from X, is an alkaline metal; and (c) reacting $R_1MR_3$ with $M_1(R_2)_4$ to obtain the metallocene complex of claim 1 represented by formula (I):

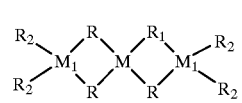

(I)

wherein
M1 is a Group IVB metal element, and
$R_2$ is selected from the group consisting of $-N(CH_3)_2$, $-N(C_2H_5)_2$, halogen, alkoxy, $-(C=O)NH_2$, and $C_{1-12}$ hydrocarbyl group.

7. The metallocene complex as claimed in claim 1, wherein M is germanium.

* * * * *